United States Patent [19]

Pariza et al.

[11] Patent Number: 6,060,304
[45] Date of Patent: May 9, 2000

[54] METHOD OF PRODUCING CONJUGATED FATTY ACIDS

[75] Inventors: Michael W. Pariza; Xiao-Yun Yang, both of Madison, Wis.

[73] Assignee: Wisconsin Alumni Research Foundation, Madison, Wis.

[21] Appl. No.: 09/170,505

[22] Filed: Oct. 13, 1998

Related U.S. Application Data

[60] Division of application No. 08/759,773, Dec. 3, 1996, Pat. No. 5,856,149, which is a continuation-in-part of application No. 08/458,956, Jun. 2, 1995, Pat. No. 5,674,901, which is a continuation-in-part of application No. 08/456,988, Jun. 1, 1995, abandoned.

[51] Int. Cl.$^7$ ................................ C12N 1/20; C12P 7/64
[52] U.S. Cl. ........................ 435/252.9; 435/134; 435/853
[58] Field of Search ................................ 435/252.9, 853, 435/134

[56] References Cited

U.S. PATENT DOCUMENTS

| | | |
|---|---|---|
| 4,603,142 | 7/1986 | Burger et al. . |
| 4,868,001 | 9/1989 | Maruta . |
| 4,888,326 | 12/1989 | Horrobin . |
| 5,017,614 | 5/1991 | Pariza et al. . |
| 5,070,104 | 12/1991 | Pariza et al. . |
| 5,162,337 | 11/1992 | Elbrecht et al. . |
| 5,208,356 | 5/1993 | Pariza et al. . |
| 5,428,072 | 6/1995 | Cook et al. . |
| 5,430,066 | 7/1995 | Cook et al. . |
| 5,504,114 | 4/1996 | Cook et al. . |
| 5,554,646 | 9/1996 | Cook et al. . |
| 5,674,901 | 10/1997 | Cook et al. . |

FOREIGN PATENT DOCUMENTS

| | | |
|---|---|---|
| 0 524 796 A1 | 7/1992 | European Pat. Off. . |
| 0 579 901 A1 | 3/1993 | European Pat. Off. . |
| 0 641 562 A1 | 9/1994 | European Pat. Off. . |
| WO 96/06605 | 5/1995 | WIPO . |
| WO96/38137 | 3/1996 | WIPO . |

OTHER PUBLICATIONS

Begin, M.E., et al., "Plasma Fatty Acid Levels in Patients with Acquired Immune Deficiency Syndrome and in Controls," *Prostaglandins Leukotrienes and Essential Fatty Acids*, 37:135–137 (1989).

Chin, Sou F., et al., "Conjugated Linoleic Acid (9,11–and 10,12–Octadecadienoic Acid) Is Produced in Conventional but Not Germ–Free Rats Fed Linoleic Acid [1,2]," *Nutrient metabolism*, pp. 694–701 (1994).

Chin et al., "Synthesis of CLA by Intestinal Microorganisms," *FASEB J.* 7, A169 (1993).

Chin et al., "Synthesis of CLA by Intestinal Microorganisms," *Food Research Institute*, 1992 Annual Report, p. 139–140.

Cook, Mark E., "Exogenous Antigen Challenge and Its Effect on Nutrient Metabolism," *Proceedings American Association of Swine Practitioners 25th Annual Meeting* (1994).

Cook, et al., "Immune Modulation by Altered Nutrient Metabolism: Nutritional Control of Immune–Induced Growth Depression: Symposium: The Microenvironment of Immune Tissue," *Poultry Science*, 72:1301–1305 (1993).

Das, U.N., "Can Essential Fatty Acid Deficiency Predispose to AIDS?", *Can. Med. Assoc. J.*, 132:900–902 (Apr. 15, 1995).

Eyssen et al., "Biotransformation of Linoleic Acid and Bile Acids by Eubacterium Lentum," *Applied and Environmental Microbiology*, 47:39–43 (1984).

Fairbank et al., "Octadeca–911 Dienoic Acid in Diagnosis of Cervical Intraepithelial Neoplasia," *Lancet* p. 329 (1988).

Fujimoto et al., "Biohydrogenation of Linoleic Acid by Anaerobic Bacteria Isolated from Rumen," *Biosci. Biotech, Biochem*, 57:1026–1027 (1993).

Ha, Y.L., et al., Anticarcinogens from fried ground beef: heat–altered derivatives of linoleic acid, *Carcinogenesis*, 8(12):1881–1887 (1987).

Ha, Y.L., et al., Newly Recognized Anticarcinogenic Fatty Acids: Identification and Quantification in Natural and Processed Cheeses, *J. Agric. Food Chem.*, 37(1):75–81 (1989).

Haumann, B., "Conjugated Linoleic acid offers research promise," *Inform.* 7:152–159 (1996).

Ip et al., "Mammary Cancer Prevention by Conjugated Dienoic Derivative of Linoleic Acid," *Cancer Research*, 51,6118–6124 (1991).

Jack et al., "Serum octadeca–9, 11 dienoic acid—an assay of free radical activity or a result of bacterial production?," *Clinica Chimica Acta*, 224:139–146 (1994).

Kemp et al., "The Hydrogenation of Unsaturated Fatty Acids by Five Bacterial Isolates from the Sheep Rumen, Including a New Species," *Journal of General Microbiology*, 90:100–114 (1975).

Kepler et al., "Biohydrogenation of Unsaturated Fatty Acids," *The Journal of Biological Chemistry*, 245:3612–3620 (1970).

Klein, A., et al., "Process of HIV Infection And Changes in The Lipid Membrane Structure of CD4+Cells," *AIDS*, 6(3):332–333 (1992).

Kohn, A., et al., "Unsaturated Free Fatty Acids Inactivate Animal Enveloped Viruses," *Archives of Virology*, 66:301–307 (1980).

Kumar, G. Sravan, et al., "Effect of n–6 and n–3 Fatty Acids on the Proliferation of Human Lymphocytes and Their Secretion of TNF–a and IL–2 in Vitro," *Nutrition Research*, 12:815–823 (1992).

(List continued on next page.)

*Primary Examiner*—Herbert J. Lilling
*Attorney, Agent, or Firm*—Quarles & Brady LLP

[57] ABSTRACT

A method for producing a cis-9, trans-11 fatty acid from a fatty acid containing double bonds in the cis-configuration at positions 9 and 12, includes the step of combining a Lactobacillus microorganism with free fatty acids in a fermentation process. The conjugated fatty acid products can include, for example, cis-9, trans-11 conjugated linoleic acid (CLA).

3 Claims, No Drawings

OTHER PUBLICATIONS

Lee et al., "Conjugated linoleic acid and atherosclerosis in rabbits," *Atherosclerosis*, 108:19–25 (1994).

The Merck Index, Tenth Edition (1983), p. 790.

Michel, et al., "Interaction of Conjugated Dienoic Derivatives of Linoleic Acid with β–Carotene on Cellular Host Defense," *Fed. Am. Soc. Exp. Biol. J.*, 6:A1102 (1992).

Miller, et al., "Feeding Conjugated Linoleic Acid to Animals Partially Overcomes Catabolic Response Due to Endotoxin Injection," *Biochemical and Biophysical Research Communication*, 198(3):1107–1112 (1994).

Mills et al., "Hydrogenation of $C_{18}$ Unsaturated Fatty Acids by Pure Cultures of A Rumen Micrococcus," *Aust. J. Biol. Sci.*, 23:1109–1113 (1970).

Nicolosi et al., "Dietary Conjugated Linoleic Acid Reduces Aortic Fatty Streak Formation Greater Than Linoleic Acid in Hypercholesterolemic Hamsters," *Circulation*, 88(suppl):24–58 (1993).

Pariza, M.W., *Food Research Institute 1988 Annual Fall Meeting*, (Oct. 12, 1988).

Peck, Michael D., et al., "The Esterified Plasma Fatty Acids Profile Is Altered in Early HIV–1 infection," *Lipids*, 28(7):593–597 (1993).

Thompson et al., "Measurement of The Diene Conjugated Form of Linoleic Acid in Plasma by High Performance Liquid Chromatography: A Questionable Non–Invasive Assay of Free Radical Activity?," *Chem. Biol. Interactions*, 55:357–366 (1985).

Uchida, K., "Occurrence of Conjugated Dienoic Fatty Acids in The Cellular Lipids of Pediococcus homari," *Agr. Biol. Chem.*, 39(2):561–563 (1975).

Verhulst et al., "Isomerization of Polyunsaturated long Chain Fatty Acids of Propionibacteria," *System. Appl. Microbiol.*, 9:12–15 (1987).

Verhulst et al., "Biohydrogenation of Linoleic Acid by Clostridium sporogenes, Clostridium bifermentans, Clostridium sordellii and Baceriodes sp.," *FEMS Microbiology Ecology*, 31:255–259 (1985).

METHOD OF PRODUCING CONJUGATED FATTY ACIDS

CROSS-REFERENCE TO RELATED APPLICATIONS

This application is a division of U.S. application Ser. No. 08/759,773, filed Dec. 3, 1996 now U.S. Pat. No. 5,856,149, which is a continuation-in-part of U.S. application Ser. No. 08/458,956, filed Jun. 2, 1995, U.S. Pat. No. 5,674,901, which is a continuation-in-part of application Ser. No. 08/456,988, filed Jun. 1, 1995, abandoned.

STATEMENT REGARDING FEDERALLY SPONSORED RESEARCH OR DEVELOPMENT

Not applicable.

BACKGROUND OF THE INVENTION

Linoleic acid is an 18 carbon molecule that contains double bonds in the cis-9, cis-12 configuration. Conjugated linoleic acid (CLA) is a general term for a set of positional and geometric isomers of linoleic acid that possess conjugated double bonds, in the cis or trans configuration, at positions 9 and 11 or at positions 10 and 12. CLA occurs naturally in a wide variety of foods, especially in foods such as cheese that are derived from ruminant animals. Ha, Y. L., N. K. Grimm and M. W. Pariza, Carcinogenesis, Vol. 8, No. 12, pp. 1881–1887 (1987); Ha, Y. L., N. K. Grimm and M. W. Pariza, *J. Agric. Food Chem.*, Vol. 37, No. 1, pp. 75–81 (1987).

CLA is now recognized as a nutritional supplement and an effective inhibitor of epidermal carcinogenesis and forestomach neoplasia in mice, and of carcinogen-induced rat mammary tumors. CLA can prevent adverse effects caused by immune stimulation in chicks, mice and rats, and can decrease the ratio of low density lipoprotein cholesterol (LDL-cholesterol) to high density lipoprotein cholesterol (HDL-cholesterol) in rabbits fed an atherogenic diet. CLA also reduces body fat in mouse, rat and chick models. The effective behavior of CLA in such animal systems suggests similar benefit when provided in the human diet. In contrast, linoleic acid, the precursor of CLA is associated with enhancing mammary cancer in rodents.

Methods of using CLA are described in issued U.S. Pat. Nos. 5,017,614; 5,070,104; 5,208,356; 5,428,072; 5,430,066; 5,504,114, and 5,554,646.

Linoleic acid can be converted to CLA by chemical methods (American Oil Chemists' Society Official Method Cd 7–58, pages 1–11, American Oil Chemists' Society, Champaign, Ill. (1973), or by enzymatic isomerization. The non-toxic salts of the free CLA acids may be made by reacting the free acids with a non-toxic base. Natural CLA may also be prepared from linoleic acid by the biological action of $\Delta^{12}$-cis, $\Delta^{11}$-transisomerase from a harmless microorganism such as *Butyrivibrio fibrisolvens*, a strictly anaerobic rumen bacterium, that produces both a cis-9, trans-11 CLA isomer and a cis-9, trans-11, cis-15 linolenic acid isomer as intermediates in the biohydrogenation of linoleic acid and linolenic acid, respectively. Kepler, C. R., et al., *J. B. C.* 245:3612–3620 (1970); see also Kemp, P. et al., *J. Gen. Microbiol.* 90:100–114 (1975), Mills, S. C. et al.,*Aust. J. Biol. Sci.* 23:1109–13 (1970), Verhulst, A. et al., *FEMS Microbiol. Ecol.* 31:255–259 (1985), Fujimoto, K. et al., *Biosci. Biotech. Biochem.* 57:1026–1027 (1993), and Eyssen H. and A. Verhulst, *Appl. Environ. Microbiol.* 47:39–43 (1984). Jack, C. I. et al., Clinica Chimica Acta 224:139–146 (1994) purport to identify a large number of bacteria that convert linoleic acid into CLA. However, no reliable analytical methodology was presented. It is more likely that linoleic acid was oxidized rather than converted to CLA. Harmless microorganisms in the intestinal tracts of rats and other monogastric animals may also convert linoleic acid to CLA (S. F. Chin, W. Liu, K. Albright and M. W. Pariza, 1992, FASEB J.6:Abstract #2665). The presence in rumen of bacteria that possess linoleate isomerase, such as *B. fibrisolvens*, could explain the high concentration of CLA in tissues obtained from ruminant animals. *B. fibrisolvens* is not commercially useful to produce CLA from its free fatty acid precursor because it is a very strict anaerobe that is difficult to grow, even under laboratory conditions. In addition, *B. fibrisolvens* has an undesired reductase activity that converts the active products to other compounds. Other rumen bacteria are known to hydrogenate cis, cis linoleic acid isomers having double bonds at positions 5 and 8, 8 and 11, 11 and 14 to octadecanoic acid (Kemp, P. and Lander, D. J., *Brit. J. Nutr.* 52:171 (1984)).

Nicolosi, R. J. et al, "Dietary Conjugated Linoleic Acid Reduces Aortic Fatty Streak Formation Greater than Linoleic Acid in Hypercholesterolemic Hamsters" Circulation 88 (suppl.), 2458 (1993), and Lee, K. L. et al. "Dietary Conjugated Linoleic Acid and Atherosclerosis in Rabbits" *Atherosclerosis* 108:19–25 (1994) established that CLA inhibits atherosclerosis in rabbits and hamsters.

Fairbank, J. et al., *The Lancet* p. 329, Aug. 6, 1988, reported detecting cis, trans isomers of 18:2(9,11) in cultures of Lactobacillus. However, this paper presented no standards, and, given the difficulties inherent in sorting out bacterial metabolism, thus included no credible evidence for making CLA using a bacterial system. This report was refuted by Thompson, S. and M. T. Smith, *Chem. Biol. Interactions J.* 55:357–366 (1985), which showed that a method described by Fairbank did not produce authentic CLA, but rather oxidized linoleic acid.

Uchida, K., *Apr. Biol. Chem.* 39:561–563 (1971) describes a strain of Pediococcus that synthesizes certain unspecified CLA isomers de novo and deposits them in its membrane. The strain does not use linoleic acid as a substrate for a linoleate isomerase enzyme. Moreover, the strain produces numerous isomers. Even if one is active, it represents too small a fraction of the total production of conjugated fatty acids to make the strain commercially practical.

Verhulst, A. et al., *System. Appl. Microbiol.* 9:12–15 (1987) describes the production of trans-10, cis-12 CLA by *Propionibacterium acnes*. This organism is a pathogen that includes a reductase that reduces the useful trans-10, cis-12 product to other non-CLA fatty acid products.

Of the various positional and geographic isomers present in CLA, the cis-9, trans-11 isomer is believed to be an active form, at least for the anticarcinogenic activity of CLA. Between 76 and 92% of the CLA isomers in uncooked meat is in the cis-9, trans-11 configuration. In processed plant oils, about 42% of the isomers were in the cis-9, trans-11 configuration and another 42% were in the trans-10, cis-12 configuration, as was the case in CLA prepared chemically from linolic acid. The trans-10, cis-12 CLA isomer may also have biological activity of the type described, but it has not been possible to prepare quantities of this isomer enzymatically for testing. It is also thought that CLA is not unique in this ability, but rather that cis-9, trans-11 and trans-10, cis-12 isomers of other fatty acids will have comparable biological activities.

It is known that linoleic acid can be efficiently converted to CLA when the linoleic acid is provided in the form of free fatty acid, rather than as a triglyceride.

It would be desirable to obtain a microorganism capable of producing the active isomer or isomers of CLA and other conjugated fatty acids, where the organism is easily grown and used and is food-safe.

BRIEF SUMMARY OF THE INVENTION

We have discovered a method for forming fatty acids that have conjugated double bonds in the cis-9, trans-11 configuration, and may have other double bonds as well. In the method, an unconjugated free fatty acid having a pair of double bonds in the cis-configuration at carbon positions 9 and 12 is exposed to a Lactobacillus (or membrane preparation therefrom) that is shown herein to contain a linoleate isomerase activity that can convert free linoleic acid into conjugated linoleic acid. The cis-9, trans-11 fatty acids thus produced can have biological activities of the type recognized in the art for cis-9, trans-11 CLA. The Lactobacillus is readily grown and maintained in anaerobic culture. Conditions for directing production of the preferred cis-9, trans-11 isomers are described herein.

The linoleate isomerase of the organism described herein requires the fatty acid to have a dissociated carboxyl group and unconjugated double bonds at positions 9 and 12 (e.g., $18:2\Delta^{9,12}$, where 18 refers to the number of carbons in the fatty acid, 2 refers to the number of double bonds, and 9,12 indicate the positions of the double bonds). The activity of the organism is reduced by the presence of an extra double bond at position 6 (see $18:3\Delta^{6,9,12}$), but is promoted by an extra double bond at position 15 (see $18:3\Delta^{9,12,15}$). A fatty acid having double bonds at both positions 6 and 15 (octadecatetraenoic acid) was consumed faster than gamma-linolenic acid, but slower than linoleic acid.

A suitable strain is a Gram positive aerobic Lactobacillus organism that can convert linoleic acid mainly to a cis-9, trans-11 CLA isomer without producing the trans-10, cis-12 isomer or the cis-10, cis-12 isomer, thereby indicating that the linoleate isomerase of the organism acts specifically on cis-12, rather than on the cis-9 double bond of the fatty acid.

It will be apparent to those skilled in the art that the forementioned objects and other advantages may be achieved by the practice of the present invention.

BRIEF DESCRIPTION OF THE SEVERAL VIEWS OF THE DRAWINGS

Not applicable

DETAILED DESCRIPTION OF THE INVENTION

In one aspect, the present invention is a method for converting a fatty acid having unconjugated double bonds at positions 9 and 12 into a fatty acid having conjugated cis-9, trans-11 double bonds. In a second aspect, the present invention is an organism that can accomplish the conversion.

In the method of the present invention, an unsaturated free fatty acid containing cis double bonds at the 9 and 12 positions and a dissociated carboxyl group is combined with a linoleate isomerase to produce primarily an isomer of the fatty acid having conjugated double bonds and a cis-9, trans-11 configuration. The conjugated fatty acids thus produced are stable and can be extracted from the cell culture medium.

The linoleate isomerase, a membrane-bound enzyme, can be provided in the form of whole bacterial cells or as a cell membrane preparation obtained from whole bacterial cells. The cells are preferably grown to early stationary phase before being harvested for use in the method.

The reaction between the linoleate isomerase of the cells and the free fatty acids can be accomplished at a temperature ranging from about 4° C. to about 60° C., preferably 4° C. to 12° C., and for a time (e.g., 1–24 hours, preferably 1–5 hours, more preferably about 3 hours) sufficient to produce a conjugated fatty acid product. The Examples, below, provide guidance on the amount of time to accomplish the conversion. Neither the enzyme activity, nor the ratio of isomers produced, is affected by the presence of oxygen. The conversion reaction medium can be any that permits maintenance of the organism and its membrane bound linoleate isomerase activity, and is preferably a buffer having a pH in the range of 7.4 to 8.8, and more preferably between 8.0 and 8.8, most preferably about 8.5. Between pH 5.5 and 7.4, less conjugated fatty acid is produced, although slightly more fatty acid is produced at the low end of that range. Under preferred conditions, and in the presence of sufficient free fatty acid, 7.8 mg of conjugated fatty acid has been produced per gram of cells.

It is envisioned that the enzyme may be obtained in purified form, either from the membrane, or by production using the available techniques of molecular biology and recombinant DNA.

The production in the method of a fatty acid isomer having a single conjugated double bond is characterized by an absorption peak at 233–234 nm. Isomers produced in the method can be distinguished from one another by gas chromatography. At least 50%, preferably at least 80%, more preferably at least 90%, still more preferably at least 95%, and more preferably 98–99%, of the fatty acid isomers initially produced by the enzyme from 18 carbon fatty acids are in the cis-9, trans-11 configuration. The negligible remainder of the isomers produced are cis-9, cis-11 and trans-9, trans-11, the latter being a conversion product of less than 10%, preferably less than 5%, of the major cis-9, trans-11 isomer. Trans-10, cis-12 and cis-10, cis-12 fatty acid isomers are not detected, nor are trans-9, cis-11 and cis-9, cis-11 isomers. Cis-9, trans-11 isomers of C-18 fatty acids are biologically active. Other isomers may also have biological activity and are found in commercial preparations of CLA. The high level of the biologically active cis-9, trans-11 isomer in preparations made according to the present invention can be advantageous for certain applications such as anticarcinogenic activity, in that it raises the specific biological activity of the conjugated fatty acid isomer preparation produced in the method. In view of the demonstrated functional benefits of the cis-9, trans-11 CLA isomer, it is anticipated that the cis-9, trans-11 isomers of other 18 carbon fatty acids will have similar activities. The same holds true for other fatty acids of other lengths, except insofar as the cis, trans conjugated bonds will be in positions other than 9 and 11, because of the different fatty acid chain lengths.

The conjugated fatty acids obtained by the practice of the described method of preparation may be free or bound chemically through ester linkages. The product is heat stable and can be used as is, or dried and powdered. The conjugated fatty acids are readily converted into a non-toxic salt, such as the sodium or potassium salt, by reacting chemically equivalent amounts of the free acid with an alkali hydroxide at a pH of about 8 to 9.

It is also envisioned that advantageous conjugated fatty acids can be supplied in milk or milk products naturally enriched with the fatty acids by adding a source of free linoleic acid and the harmless bacteria described herein to milk and incubating the mixture for about 1 hour at 37° C. or until the linoleic acid is converted into CLA.

The conjugated fatty acids and their non-toxic derivatives, such as the non-toxic salts, in addition to being added to an animal's feed or human food or formed in situ can be administered in the form of pharmaceutical or veterinary compositions, such as tablets, capsules, solutions or emulsions to the animal or the humans. The exact amount to be administered, of course, depends upon the form employed, the route of administration, and the nature of the animal's or human's condition. Generally, the amount employed as a pharmaceutical will range from about one part per million (ppm) to about 10,000 ppm in the animal's or human's diet. However, the upper limit of the amount to be employed is not critical because the products are relatively non-toxic and are normal constituents of the human diet (including human breast milk). The amounts to be added to a conventional animal feed or human's food as an additive can range from 0.01% to 2.0% or more by weight of the animal's or human's food.

The preferred pharmaceutical and veterinary compositions of CLA contain the non-toxic sodium or potassium salt of CLA in combination with a pharmaceutical diluent. When the compositions are solutions or suspensions intended for oral administration the diluent will be one or more diluents, such as lactose or starch, and the product will be a tablet, capsule or liquid. When the compositions are solutions or suspensions intended for parenteral administration the preferred diluent will be Sterile Water for Injection U.S.P.

In a second aspect, the invention is a substantially pure preparation of a Lactobacillus strain having the desired linoleate isomerase activity. A "substantially pure preparation" is derived from a single bacterial isolate and comprises primarily (more than about 50% preferably more than 90%) individual cells having an ability to perform the enzymatic conversion described in the method. A preparation can be considered substantially pure for purposes of this application if, when brought into contact with a free fatty acid, conversion occurs to the extent noted above.

A preferred bacterial cell having the desired linoleate isomerase activity is *Lactobacillus reuteri* PYR8 (previously denoted PLR8), deposited with the American Type Culture Collection, 12301 Parklawn Drive, Rockville, Md. 20852 USA and accorded Accession Number ATCC 55739. The preferred microorganism is a Gram positive, catalase-negative, bacteria which forms non-motile rods. It grows at 45° C. but not at 15° C., and can be distinguished from related *L. fermentum* by G+C content. *L. fermentum* has a G+C content of 52–54%, whereas L. reuteri has a G+C content of 40–42.3%. The G+C content of ATCC 55739 is 42.25%. The two can also be distinguished by differences in murein type, by differences in electrophoretic mobility of L-lactate dehydrogenase proteins, and by difference in cellular C18:1 isomer number. A cellular fatty acid profile of PYR8 was examined along with those of one strain of *L. reuteri* (ATCC 23272), and two strains of *L. fermentum* (ATCC 14931 and ATCC 23271) using GC. The final detection temperature was lowered to 180° C. to separate all peaks. The two ATCC Lactobacillus species differed in their isomer number of C18:1. *L. reuteri* had three isomers while *L. fermentum* had only two isomers. PYR8 had three isomers of C18:1, further demonstrating that the isolate was properly assigned to *L. reuteri*.

Detailed biochemical characteristics of the *L. reuteri* organism are set forth in Table I. With this strain, the extent of production of conjugated fatty acids is directly proportional to the cell biomass synthesis, suggesting that the isomerase is an accumulated enzyme and is not a functional enzyme for cell growth.

TABLE I

| Biochemical characteristics | | | |
|---|---|---|---|
| Indole production | − | Cellobiose | − |
| N-Acetylglucosaminidase | − | Esculin pH | − |
| α-Glucosidase | + | Esculin hydrolysis | − |
| α-Arabinosidase | − | Glycogen | − |
| β-Glucosidase | + | Lactose | weak |
| α-Fucosidase | − | Maltose | weak |
| Phosphatase | − | Mannitol | − |
| α-Galactosidase | + | Melezitose | − |
| β-Galactosidase | + | Raffinose | weak |
| Indoxyl-acetate | + | Rhamnose | weak |
| Arginine utilization | + | Salicin | − |
| Leucine aminopeptidase | + | Xylose | − |
| proline aminopeptidase | − | Nitrate utilization | + |
| Pyroglutamic acid arylamidase | − | Hemolysis | − |
| | | Bile green utilization | − |
| Tyrosine aminopeptidase | − | | |
| Arginine aminopeptidase | + | Fructose | + (massive gas) |
| Alanine aminopeptidase | + | Glucose | + (acid + gas) |
| Histidine aminopeptidase | + | Meat | − |
| Phenylalanine amino-peptidase | + | Motility | − |
| | | Growth at 15° C. | − |
| Glycine aminopeptidase | − | Growth at 45° C. | + |
| Catalase | − | | |

The *L. reuteri* isolate is a distinct biotype from other *L. reuteri* isolates in that it possesses the characteristic linoleate isomerase activity that is not present in, for example, ATCC 23272, another *L. reuteri* isolate from human feces. Also, this isolate does not produce reuterin.

To obtain a suitable enzyme preparation, the organism can be grown to early stationary phase before being harvested (e.g., by centrifugation) and then weighed. The cells are re-suspended in a physiological buffer (e.g., Tris-maleate at 0.1 Molar, pH 5.4). Greater conversion is observed when the cells are suspended at a ratio of 1 part bacteria to at least about 10–15 parts of aqueous buffer. The yield of conjugated fatty acids decreases significantly if the system includes less than 10–15 parts water. The conjugation can be achieved by combining the cells with the free fatty acids with gentle stirring until the conjugated product is produced.

The linoleate isomerase of ATCC 55739 appears to act specifically on fatty acids having double bonds at positions 9 and 12 to produce primarily products having conjugated cis-9, trans-11 double bonds, but within that constraint, appears to act upon all such fatty acids. The known fatty acids have either 12, 14, 16, or 18 carbons. The invention would also apply to fatty acids that can be produced by carbon chain elongation, which can be achieved naturally or using methods known to the art. Elongation can occur before or after enzymatic formation of the conjugated double bonds according to the present invention. Thus, products having conjugated cis, trans double bonds at positions other than 9 and 11 can be formed by practicing the method of the present invention on, for example, an 18 carbon fatty acid and subsequently altering the length of the fatty acid chain. References herein to producing cis-9, trans-11 products are to be understood to include such other products. The cellular fatty acids of the treating strain can also increase when the strain is combined with free fatty acids.

It is economical to prepare free fatty acids for use in the method by hydrolysing a plant oil using, for example, lipase. The fatty acid can be hydrolyzed with or without a stabilizing emulsifier such as 2% lecithin, and can be sonicated for better distribution. Yield may be higher if an emulsifier is included or if the reaction occurs under anhydrous conditions. A working stock of the fatty acids can be prepared by diluting the fatty acid preparation in a buffer such as Tris-HCl (0.1M, pH 8.5). It is advantageous to utilize an inexpensive, edible plant oil rich in the desired fatty acid as the source of free fatty acids. For example, corn oil, rich in linoleic acid ($18:3\Delta^{9,12,15}$), sunflower oil, linseed oil or evening primrose oil, which is rich in gamma-linolenic acid ($18:3\Delta^{6,9,12}$), are all suitable. Other suitable fatty acids include octadecatetraenoic acid ($18:4\Delta^{6,9,12,15}$) and alpha-linoleic acid.

The Lactobacillus shows no activity against unsaturated fatty acids lacking double bonds at both positions 9 and 12.

Inactive substrates include oleic acid ($18:1\Delta^{9}$), octadecanoic acid ($18:1\Delta^{2}$), eicosadienoic acid ($20:2\Delta^{11,14}$), eicosatrienoic acid ($20:3\Delta^{8,11,14}$), eicosatrienoic acid ($20:4\Delta^{5,8,11,14}$), and arachidonic acid ($20:4\Delta^{5,8,11,14}$).

Table II provides a list of substrates tested with ATCC 55739.

TABLE II

List of the tested substrate and the major putative products of the linoleate isomerase of *L. reuteri* PYR8

| Substrates[a] | Major Products |
| --- | --- |
| Oleic acid ($18:1\Delta^{9}$) | None |
| Octadecanoic acid ($18:1\Delta^{12}$) | None |
| Linoleic acid ($18:2\Delta^{9,12}$) | cis9, trans11 isomer[b] |
| Gamma-linolenic acid ($18:3\Delta^{6,9,12}$) | cis6, cis9, trans11 |
| Alpha-linolenic acid ($18:3\Delta^{9,12,15}$) | cis9, trans11, cis15 |
| Octadecatetraenoic acid ($18:4\Delta^{6,9,12,15}$) | cis6, cis9, trans11, cis15 |
| Eicosadienoic acid ($20:2\Delta^{11,14}$) | None |
| Eicosatrienoic acid ($20:3\Delta^{8,11,14}$) | None |
| Eicosatrienoic acid ($20:3\Delta^{11,14,17}$) | None |
| Arachidonic acid ($20:4\Delta^{5,8,11,14}$) | None |

[a]Each substrate (0.2 mg) was reacted with the cells (20 mg) of *L. reuteri* PYR8, and product was analyzed by GC, as described in methods.
[b]As a known product.

The invention will be more fully understood upon consideration of the following non-limiting Examples.

EXAMPLES

Isolation and Characterization of Bacteria

Conventional rats, after being fed 5% linoleic acid for 4 to 8 weeks, have a significantly higher CLA concentration in their tissue than germ-free rats on the same diet. Based on this observation, we attempted to isolate CLA-producing bacterial strains from the intestinal tracts of conventional rats.

Whole intestinal tract of two conventional rats were taken and opened. The tissue of each rat intestinal tract was soaked in 50 ml of potassium phosphate buffer (0.05 M, pH 7.0) for 30 minutes. The suspension, containing rat intestinal microflora, was streaked on Brain Heart Infusion (Difco Laboratories, Detroit, Mich.), Lactobacilli MRS (BBL Microbiology System, Cockeysville, Md.) and potato dextrose agar (BBL Microbiology System) plates. Two sets of plates were incubated under aerobic and anaerobic conditions at 37° C. Fifteen colonies isolated from aerobic incubation and 30 colonies from anaerobic incubation at 37° C. were picked for further evaluation.

Colonies that appeared on the plates were picked and cultured again in the same media. The cells were collected by centrifugation at 4500 g for 20 minutes, suspended in 0.1 M Tris-maleate buffer (pH 7.5), and adjusted to an absorbance of 1.0 at 600 nm. Linoleic acid stock (10 mg/ml) was prepared in 1,3-propanediol and stored in a −20° C. freezer.

The 45 cultures in total were screened for conversion of linoleic acid to CLA with HPLC and GC. Cell suspensions were added to the fatty acid stock. The reaction was incubated for 40 minutes in a 37° C. water bath or at 4° C. for two hours. Suitable controls containing only cells and only fatty acid, respectively, were also tested.

Fatty acids were extracted with chloroform:methanol (2:1) and 4% KCl. Hexadecanoic acid (HDA) was added as an internal standard. The extraction mix was centrifuged at 2000 g for 5 minutes, then the chloroform fraction containing the fatty acids (bottom fraction) was removed and dried down by nitrogen gas. The fatty acids were suspended in 4% HCl in anhydrous methanol, and were methylated in a 60° C. water bath for 20 minutes. Finally, drops of double distilled water (DDW) were added to the methylation tube and hexane was used to re-extract the fatty acid. After washing twice with DDW and dehydrating by sodium sulfate, 1–2 µl of the hexane fraction was injected into a model 5890 series II gas chromatograph fitted with a model 3396A integrator (Hewlett-Packard Company, Avondale, Pa.) for fatty acid analysis. Fatty acid peaks were separated with a fused silica capillary column, 60 m by 0.32 ml I.D. with a 0.25 µm film thickness (Supelco Park, Bellefonte, Pa.).

The external standard was chemically prepared CLA that included cis-9, trans-11/trans-9, cis-11; trans-10, cis-12; cis-9, cis-11; cis-10, cis-12; and trans-9, trans-11/trans-10, trans-12 isomers. CLA in hexane was also assayed by a DU-50 series spectrophotometer (Beckman Instruments, Inc., Irvine, Calif.) at 233 nm.

Only 4 of the strains isolated from MRS under anaerobic conditions had the ability to produce CLA from the linoleic acid. Among them, one strain, grown in MRS medium and designated PYR8, was selected because it produced the highest CLA as measured by HPLC. The CLA produced by the strain was the cis-9, trans-11 form of conjugated linoleic acid. The selected strain produced the highest amount of CLA after a 36-hour incubation at 37° C.

The CLA isomers were not present in cellular lipid of PYR8, but were converted from linoleic acid added to a suspension of PYR8 cells. By comparing the retention times of the products produced in the method and the products present in authentic CLA, it was determined that PYR8 produced one major and two minor CLA isomers. The major isomer, which accounted for about 98% of the product, was cis-9, trans-11 CLA isomer. The minor products were cis-9, cis-11 and trans-9, trans-11 CLA isomers.

Several other Lactobacillus species were examined to determine whether linoleic acid isomerase activity is widespread in the genus. One strain each of *L. bulgaricus*, *L. helveticus*, *L. asodolphous*, *L. plantarum*, and *L. brevis*, and four strains of three species from ATCC: *L. murinus* from rat ATCC 35020), *L. fermentum* from bean (ATCC 14931), *L. fermentum* from human (ATCC 23271) and *L. reuteri* from human (ATCC 23272) were examined. However, none was able to convert linoleic acid to CLA.

Finally, the isolate was tested for reuterin production and *L. reuteri* ATCC 23272 was used as a positive control. The assay was conducted using a combination and modification of the methods described by Chung, et al., *Microbial Ecolocy in Health and Disease* 2:137–144 (1989) and by Talarico, et al., *Antimicrobial Agents and Chemotherapy*

32:1854–1858 (1988). Briefly, an overnight culture was inoculated (1% v/v) into 20 ml of Lactobacillus carrying medium and grown for 16 hours at 37° C. Cells were harvested by centrifugation at 4,500 g for 15 minutes and were washed twice with 50 mM sodium phosphate buffer (pH 7.5), then suspended in 5 ml of sterile 250 mM glycerol, then allowed to grow anaerobically at 37° C. for another 2–4 hours. After centrifugation, the supernatant fraction was filtered through an Acrodisc filter with 0.45 micron pore size and stored at 4° C. Reuterin production was measured by a minimum inhibitory concentration assay using $E.\ coli$ K-12 as an indicator. The supernatant fraction was serially diluted (1:2) in the MIC assay medium and 0.2 ml of $E.\ coli$ ($10^6$ CFU) was added into each 2 ml test solution. Inhibitory effect was observed after incubation at 37° C. for more than 6 hours. PYR8 did not produce reuterin, which is a broad spectrum antibiotic.

Preferred Culture Conditions

The isolate was studied to determine desirable culture conditions for cells to be used in converting fatty acids. PYR8 was inoculated (1% v/v) into 1L of MRS broth (Difco Laboratories, Detroit, Mich.). After incubation for 18, 24, 36 and 48 hrs at 37° C., cells were collected by centrifugation (4000 g for 10 minutes), weighed and suspended in 0.1M Tris-HCl buffer (pH 8.55) at a ratio of 1:10 (g/ml). For each growth time, 2 ml of the cell suspension was added to 1 ml of the same buffer containing 100 μl linoleic acid stock (15 mg/ml in 1,3-propanediol). Cells alone and linoleic acid alone were used as controls. The reaction was carried out in a cold room (4° C.) for 2 hours. CLA production increased correspondingly with increasing cell biomass. The content of cellular fatty acids increased with the age of the culture. Cells at the early stationary phase (36 hours) produced the most CLA (assayed by GC method).

TABLE III

The relationship of culture age and CLA yield by *L. reuteri* PYR8

| Culture (hours) | Biomass (g/L) | Cellular fatty acid (mg/g cells) | CLA yield[a] (mg/g cells) |
|---|---|---|---|
| 18 | 3.34 | 0.11 | 1.56 |
| 24 | 4.19 | 0.21 | 2.34 |
| 36 | 5.53 | 0.53 | 7.86 |
| 48 | 5.28 | 0.75 | 7.51 |

[a]In 3 ml of 0.1 M Tris-HCl buffer (pH 8.55) contained 1.5 mg linoleic acid and 0.2 g PYR8 cells. Reaction was carried out at 4° C. for 2 hour.

The amount of CLA produced over time in a reaction using 36 hour-old cells, determined by GC method after methylation, increased linearly from 0 minutes to 1 hour and continued to increase up to 3 hours, then plateaued. Between 4 and 24 hours, the composition of the CLA isomers changed. At 3 hours, the cis-9, trans-11 isomer constituted 96.23% of the total CLA isomers. After that, the concentration of that isomer declined gradually as the concentration of trans-9, trans-11 isomer increased, but the percentage of cis-9, cis-11 isomer did not change, indicating thea the trans-9, trans-11 isomer was derived from the cis-9, trans-11 isomer.

Thirty-six-hour cultures were diluted in 0.1M Tris-HCl (pH 8.55) buffer to 1:10, 1:15, 1:20 (w/v). Five ml of each suspension were reacted with 2.0 mg of linoleic acid for 1, 2, or 3 hours at 12° C. At 1:15, five ml were incubated with 1.0 mg, 1.5 mg, 2.0 mg and 3.0 mg of alpha-linolenic acid for 1 hour, or with 2.0 mg of gamma-linolenic acid for 1, 2, 3, 4, or 24 hours at 4° C. Fatty acids were extracted with chloroform:methanol and assayed by the GC method. At dilutions of 1:10, 1:15, and 1:20 (g cells/ml), the cultures utilized 100%, 100%, and 94% of the linoleic acid, respectively. On average, 75% of the total fatty acid produced was in the cis-9, trans-11 configuration. At 1:15, the cells converted 2.5 mg of alpha-linolenic acid in one hour, with 78% of the fatty acid being cis-9, trans-11, cis-12. The cells were unable to convert gamma-linolenic acid to cis-6, cis-9, trans-11 gamma linolenic acid in 24 hours. The rates of converting linoleic acid, alpha-linolenic acid and gamma-linolenic acid were 3.2, 8.0, and less than 0.25 mg/hour/gram cells, respectively.

It will be readily apparent to those skilled in the art that a number of modifications or changes may be made without departing from the spirit and scope of the present invention. Therefore, the invention is only to be limited by the claims.

We claim:

1. A substantially pure preparation of a Lactobacillus strain that, when combined with fatty acids having a dissociated carboxyl group and unconjugated double bonds in the cis-9, cis-12 configuration, can convert the fatty acids into conjugated fatty acids wherein at least 50% of the conjugated fatty acids comprise conjugated double bonds in the cis-9, trans-11 configuration.

2. A substantially pure preparation as claimed in claim 1 where the strain is classified as *Lactobacillus reuteri*.

3. A substantially pure preparation as claimed in claim 1 where the strain is classified as *Lactobacillus reuteri* PYR8 (ATCC 55739).

* * * * *